United States Patent [19]

Westlake, III et al.

[11] Patent Number: 5,442,968
[45] Date of Patent: Aug. 22, 1995

[54] MEMBRANE-BASED FLUID SEPARATIONS APPARATUS

[75] Inventors: Theodore N. Westlake, III; Duane K. Wolcott, both of Baton Rouge; Gary D. DeLeo, Donaldsonville, all of La.

[73] Assignee: The Dow Chemical Company, Midland, Mich.

[21] Appl. No.: 986,839

[22] Filed: Dec. 8, 1992

[51] Int. Cl.6 .................... B01D 15/00; B01D 19/00; G01N 1/10; G01N 30/96
[52] U.S. Cl. ............................. 73/863.23; 73/863.81; 210/321.74
[58] Field of Search ............... 73/19.12, 29.05, 863.23, 73/863.81; 95/151, 158; 96/151, 219, 220; 210/321.74

[56] References Cited

U.S. PATENT DOCUMENTS

| | | | |
|---|---|---|---|
| 3,483,990 | 12/1969 | Litle et al. | 210/321 |
| 3,735,558 | 5/1973 | Skarstrom et al. | 55/16 |
| 3,830,106 | 8/1974 | Gardiner et al. | 73/863.81 |
| 4,325,715 | 4/1982 | Bowman et al. | 210/321.74 |
| 4,842,736 | 6/1989 | Bray et al. | 210/321.74 |
| 4,846,977 | 7/1989 | DeVellis et al. | 210/321.74 |
| 4,902,416 | 2/1990 | Schroeder et al. | 210/321.74 |
| 5,137,637 | 8/1992 | Korin | 210/321.74 |

FOREIGN PATENT DOCUMENTS 1440963  5/1973  United Kingdom.

*Primary Examiner*—Richard E. Chilcot, Jr.
*Assistant Examiner*—George M. Dombroske

[57] ABSTRACT

A membrane-based fluid separations apparatus, comprising an outer vessel or outer vessel assembly having an opening defined therein, a probe member inserted through and secured in the opening and having a groove defined therein, and a tubular membrane supported in the groove in the probe member and defining first and second ends which can be placed in fluid communication with a source of a fluid from which a species is to be selectively removed and a desired destination for fluid from said membrane, respectively.

13 Claims, 2 Drawing Sheets

MEMBRANE-BASED FLUID SEPARATIONS APPARATUS

The present invention relates to apparatus for selectively removing a given species of material from a fluid and especially from a gas, and more particularly to membrane-based apparatus for selectively removing a given species of material from a fluid stream.

One of the primary applications of such apparatus currently is in the area of fluid drying, i.e., the removal of water from fluids and especially from carrier gases and the like for use with associated analytical instrumentation. Because of the opportunity presented for contamination by materials in the drying agent, it is very often undesirable to bring a fluid into direct contact with a conventional drying agent for removing water from the fluid. Apparatus have for this reason been developed which use a membrane to separate the fluid to be dried from the drying agent, see, e.g., U.S. Pat. No. 3,735,558 to Kertzman.

The known membrane-based dryers (of which the device in the Kertzman patent is exemplary) are configured essentially as a "tube within a tube", with a tubular membrane being disposed between two ends of a pipe and a drying agent either being disposed as a solid on the outside/shell side of the membrane or flowing as a liquid or dry gas drying agent on the shell side of the membrane.

These "tube in a tube" membrane-based dryers possess a number of significant shortcomings, however. Those having a quantity of a solid drying agent disposed around the tubular membrane are fairly inexpensive, but the solid drying agent is difficult to change, and changing the drying agent requires disassembling the dryer and stopping the flow of a gas or other fluid through the membrane. This flow stoppage causes difficulties, obviously, in those analytical instruments and apparatus which require a steady flow of a high purity dry gas thereto. The dryers employing a flowing stream of a liquid or dry gas drying agent were developed to avoid the changeout and flow stoppage problems associated with solid drying agents, but these dryers are considerably more expensive on the whole than those employing solid drying agents.

In addition, in both designs the tubular membrane must be self-supporting, which limits the length and thinness of the membrane and thus the rate of mass transfer and drying that can be achieved with such a membrane. Further, the surface of the membrane is exposed and subject to abrasion and wear by contact with the drying agent employed.

Many, if not all, of the foregoing disadvantages are shared by the known membrane-based apparatus for other (i.e., other than drying) types of separations generally.

SUMMARY OF THE PRESENT INVENTION

The present invention provides a membrane-based fluid separations apparatus which overcomes these and other shortcomings of the known membrane-based apparatus.

The membrane-based fluid separations apparatus of the present invention fundamentally comprises an outer vessel or outer vessel assembly having first and second openings defined on first and second respective ends of the vessel or vessel assembly, a removable end cap placed securely over the first opening whereby a drying or other separations agent placed or flowing within the vessel is contained by the end cap at said first end, a probe member inserted through and secured in the second opening of the vessel or vessel assembly and having a groove defined therein, and a tubular membrane supported in the groove in the probe member and defining first and second ends which can be placed in fluid communication with a source of a fluid from which a species is to be selectively removed and an intended destination for the treated fluid, respectively, for example a gas chromatograph or other associated analytical device.

The insertable nature of the membrane-supporting probe permits the continued flow therethrough of a fluid to be treated while the removable end cap is removed, and a conventional solid drying or other separations agent for example which is contained in the vessel or vessel assembly is removed and replaced through the first end of the vessel or vessel assembly. Further, as the membrane in the present dryer is externally supported in a groove rather than being self-supporting, a substantially longer and thinner-walled membrane can be used for greater mass transport and improved drying or separations capacity generally without at the same time increasing the likelihood of the membrane's being distorted, abraded, damaged etc. by contact with the drying or other separations agent.

DETAILED DESCRIPTION OF PROFFERED EMBODIMENTS OF THE INVENTION

Figure 1:
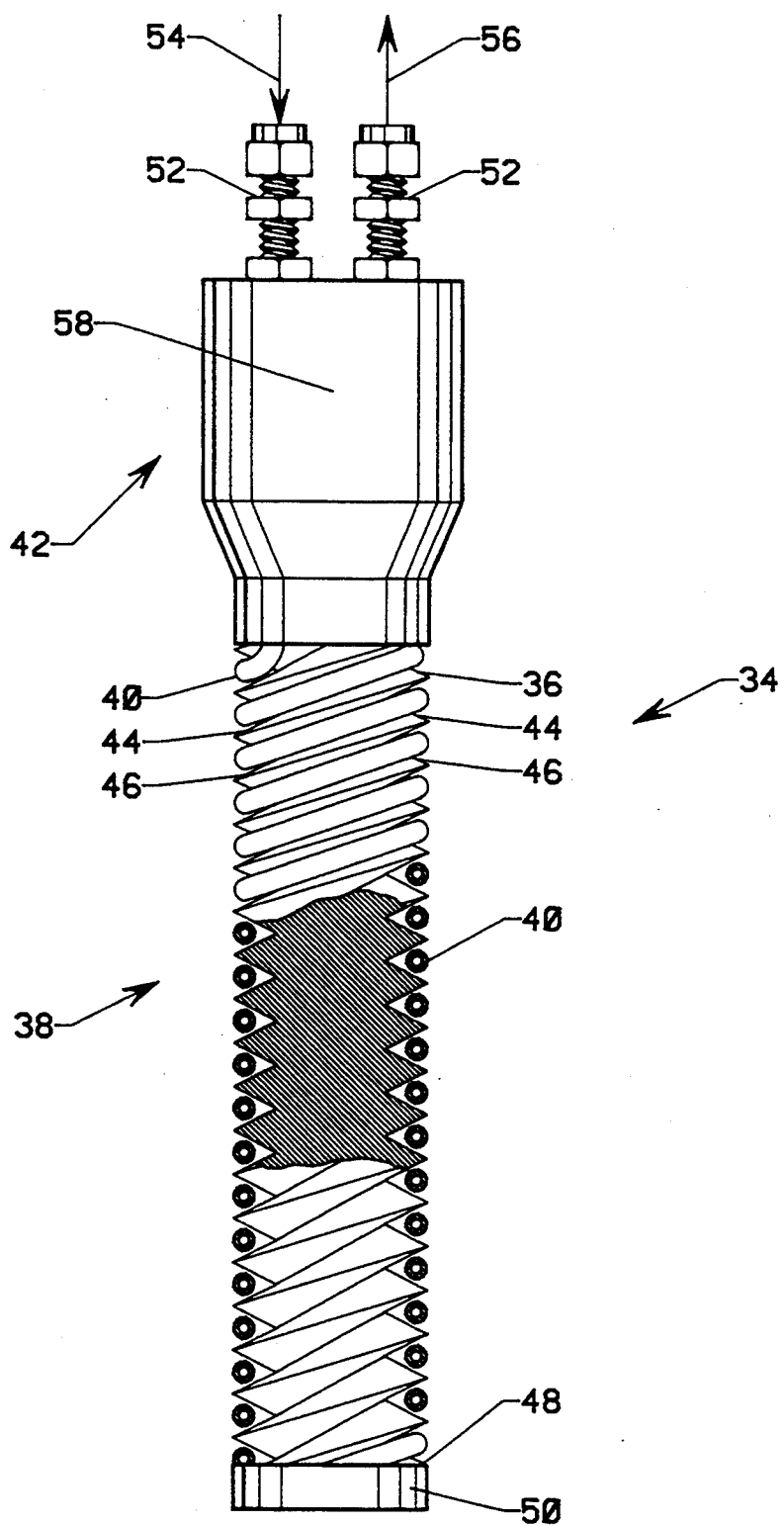
FIG. 1 is a view in partial cross-section of a preferred membrane-supporting probe for use in the membrane-based fluid separations apparatus of the present invention.
Figure 2:
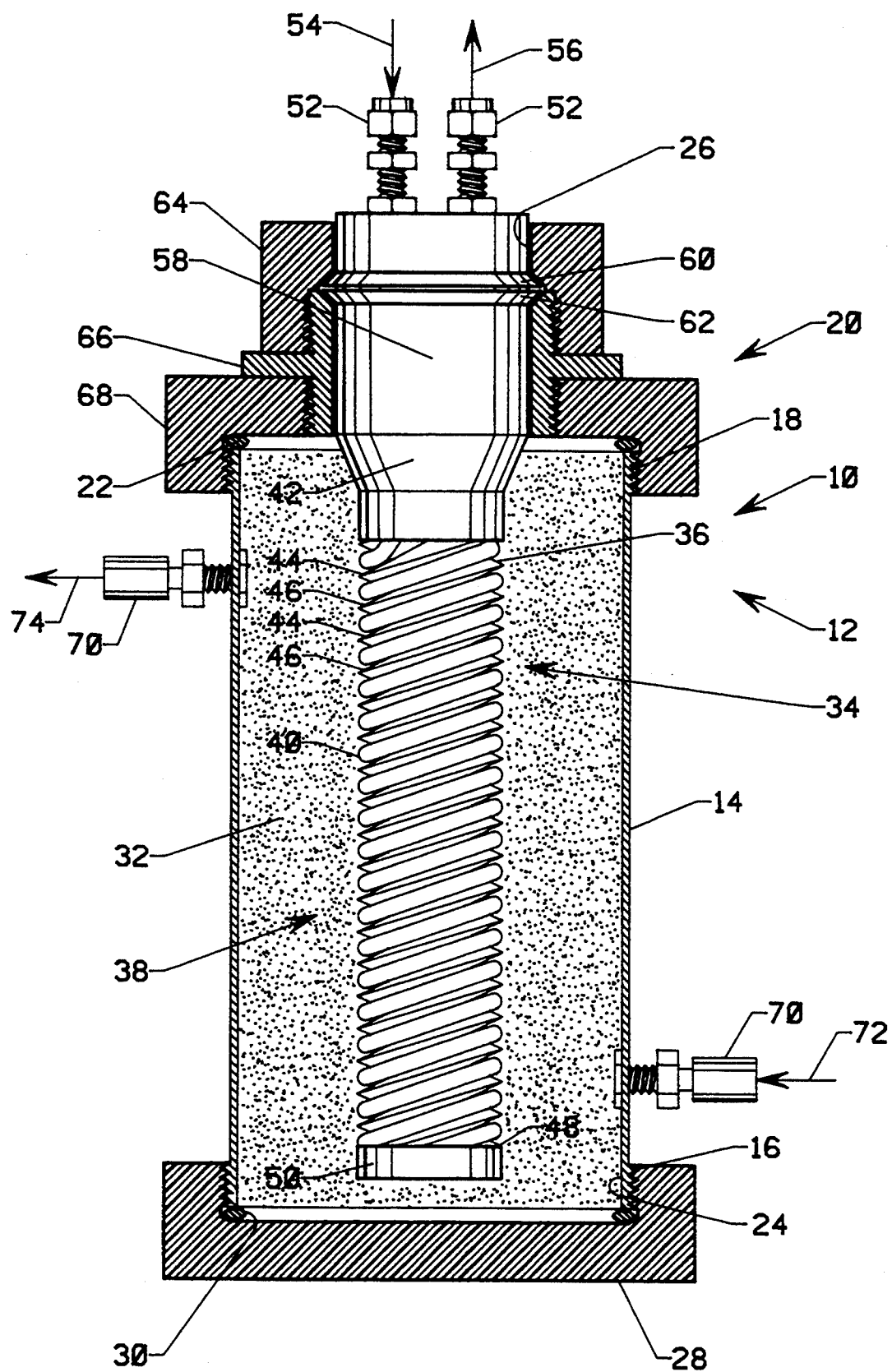
FIG. 2 depicts a preferred membrane-based fluid separations apparatus of the present invention which incorporates the probe of FIG. 1 therein, with the outer vessel assembly and removable end cap of the apparatus being shown in cross-section.

Referring now to FIGS. 1 and 2, a preferred membrane-based fluid separations apparatus 10 of the present invention is shown. Referring now to FIG. 2 in particular, the apparatus 10 comprises an outer vessel assembly 12 including a hollow cylindrical member 14 which is externally threaded at a first end 16 and at a second end 18, and further including a drilled-through tube to pipe adapter assembly 20 which screws securely onto the threaded second end 18 of the member 14. Preferably the adapter assembly 20 and the cylindrical member 14 form a gas-tight seal via an O-ring 22 or the like disposed between the adapter assembly 20 and the cylindrical member 14.

The outer vessel assembly 12 through member 14 thus defines a first opening 24 at the first end 16 of member 14 and of the assembly 12, and through an opening 26 for the "tube" in the tube to pipe adapter assembly 20 defines a smaller second opening at a second end 18 of the assembly 12.

A removable, internally-threaded end cap 28 screws securely onto the threaded first end 16 of the member 14, and like adapter assembly 20 at the second end 18 preferably forms a gas-tight seal with the member 14 via an O-ring 30 or the like disposed in end cap 28.

Where the apparatus 10 is used in a preferred application as a fluid dryer, a preferred solid, flowable drying agent 32 (for example, granular calcium or magnesium sulfate) is contained within the outer vessel assembly 12

(comprising the hollow cylindrical member 14 and adapter assembly 20) by end cap 28, and can be simply and quickly removed from the assembly 12 by unscrewing and removing end cap 28 from the first end 16 of member 14.

To provide the membrane interface with the drying agent 32, a probe member 34 is inserted through and secured in the second opening 26 as the "tube" in the drilled-through tube-to-pipe connection offered by adapter assembly 20, with the "pipe" in this case being the hollow cylindrical member 14. Probe member 34, which can be seen more clearly in FIG. 1, is preferably as described in conjunction with FIGS. 5-7 and 10 of commonly-assigned and copending U.S. Ser. No. 07/843,687, filed Feb. 28, 1992, now issued as U.S. Pat. No. 5,317,932, with such copending application being incorporated herein by reference.

In general terms, however, the probe member 34 has a groove 36 defined therein which extends longitudinally in member 14, and which preferably extends substantially from the second end 18 toward the first end 16 of the member 14 and vessel assembly 12. The groove 36 in the illustrated preferred construction of the probe member 34 arises in a double-lead flight threaded portion 38 of the member 34 which begins preferably near the second end 18, and which extends substantially over the full length of member 34.

A tubular membrane 40 is inserted through an internal channel in an unthreaded portion 42 of the member 34, traverses the length of member 34 from the second end 18 toward the first end 16 and then back toward the second end 18 via alternating flights 44 and 46 of the double-lead flight threaded portion 38, and exits from member 34 via a second internal channel in the unthreaded portion 42 of the member 34. Alternating flights 44 and 46 are for this purpose joined in communication via an S-shaped channel at an end 48 of the probe member 34. A cap 50 is screw-fastened to the probe member 34 over the S-shaped channel to contain and protect the membrane 40 therein.

Tubular membrane 40 is preferably sized so as to be fully supported in the flights 44 and 46. In this manner, the membrane 40 is fully supported over its length and can therefore be made longer and thinner-walled than if it were required to be self-supporting, while being substantially protected from abrasive contact with a drying agent 32 for example, and especially the preferred, less expensive solid drying agents.

Connector devices 52 provide a means for joining a source (not shown) of a wet fluid to be dried (whether gaseous or liquid in nature) in fluid communication with the membrane 40, as well as means for communicating the dried fluid flowing through membrane 40 to, for example, an analytical device (not shown) in need of the dried fluid. The flow of the wet fluid into the dryer 10 is represented by the flow arrow 54, while the flow of the dried fluid from dryer 10 is represented by the flow arrow 56.

Connector devices as described in U.S. Pat. No. 5,317,932 (the '932 patent) preferably each consist of a membrane support tubing insertable into the central lumens of the membrane 40, a two ferrule compression-type fitting for joining the membrane support tubing to a conventional tubing lead from an analytical device, for example, and a compression-type tube-to-tube bulkhead fitting tying the two ferrule fitting and a membrane sealing ferrule into an integrated whole. The bulkhead fitting in turn is threadedly joined to probe member 34.

The probe member 34 is preferably secured in the second opening 26 through the aforementioned conventional drilled-through "tube to pipe" adapter assembly 20 shown in FIG. 2. The probe member 34, as envisioned in the '932 patent, is possessed of a generally cylindrical, smooth shoulder portion 58. To hold the probe member 34 in place in the second opening 26, then, opposed closely-fitting collar members 60 and 62 are placed around the smooth shoulder portion 58. The uppermost collar member 60 is of the split-ring type, so that on screwing members 64, 66 and 68 tightly together the members 60 and 62 supported therebetween are compressed and the uppermost member 60 compresses the smooth shoulder portion 58 at its periphery. Those skilled in the art will recognize however that other ferrule arrangements could be used for holding the probe member 34 in place in the manner just described, depending on the intended application of the present inventive apparatus (i.e., high pressure applications versus low pressure applications).

Those skilled in the art will also recognize that other considerably different constructions could be employed for placing the probe member 34 in the hollow cylindrical member 14. For example, threads could be provided on the shoulder portion 58 of a probe member 34, and the member 34 joined to the assembly 12 via a threaded opening in an end cap at the second end 18 of member 14, with the end cap in turn being internally threaded and screwed onto the member 14 at its second end 18. Alternatively, the end cap and member 14 in such an embodiment could be consolidated into a hollow cylindrical outer vessel having a first end like the first end 16 of dryer 10, but having a second end which is closed but for a smaller threaded opening therethrough in which the member 34 can be inserted and secured.

In still other embodiments which may be appropriate for particular applications and uses of the apparatus 10, the probe member 34 could be dedicated to this use and glued, welded or otherwise affixed in an opening in an end cap, an adapter assembly or in the closed second end of an outer vessel. Still further, it may be appropriate in some circumstances to eliminate the end cap 28 over the first end 16 of the member 14, while providing an opening in an otherwise-closed second end in which the member 34 can be permanently affixed. The device would then be constructed essentially like an oil filter, and would be disposed of as a unit. It could still be possible in this type of construction to use a flow-through dessicant, it should be noted.

In the preferred embodiment of the apparatus shown in FIG. 2, the apparatus 10 having a solid drying agent 32 incorporated therein is further comprised of means for purging unwanted atmospheric gases from the outer vessel assembly 12 at least prior to placing the apparatus 10 in operation, so that a high purity of dry fluid delivery may be obtained from the apparatus/dryer 10.

This purging means may be in the form of septa needle ports, for example, or may as shown in FIG. 2 be in the form of Swagelok TM -type tube-to-pipe male connectors 70 whereby a flow of a dry purging gas may be communicated to and from the assembly 12. Corresponding flows of a purge gas into and from the dryer 10 are represented by arrows 72 and 74, respectively. In other, preferred embodiments, the connectors 70 are coupled with valves for blocking off the assembly 12 after a purging of the assembly 12 has occurred. The dry purging fluid could have a separate source, or could simply and preferably comprise a portion of the dry fluid proceeding from the dryer 10. Where a flow-through dessicant is to be employed, of course, the connectors 70 could serve as an appropriate entrance and exit for the flow-through dessicant.

Those skilled in the art will recognize that while preferred embodiments of the present invention have been described and illustrated, numerous other changes may be made thereto which are nevertheless properly considered within the scope and spirit of the present invention as defined in the claims below.

Most notably, while much of the foregoing description has focused on use of the apparatus 10 as a fluid dryer, as has previously been suggested other applications are equally possible wherein a species is selectively removed from a fluid via the membrane 40. Those skilled in the art will be well able to conceive of a number of such applications. For example, the selective removal of ammonia from a gas could be accomplished by using a silicone rubber membrane surrounded by an absorbent packing of charcoal or a material chemically reactive with ammonia, for example a low vapor pressure, phosphoric acid solution which would form ammonium phosphate with the ammonia. Carbon dioxide could be selectively removed from a gas by surrounding the membrane with Ascarite TM sodium hydroxide-coated silica from Union Carbide, which scavenges carbon dioxide selectively and reversibly. As a further example, oxygen could be removed from a fluid by surrounding the membrane with barium metal catalyst that irreversibly reacts with the oxygen to form barium oxide.

Further, while the apparatus of the present invention is most particularly adapted for use with a conventional solid drying or other separations agent and is preferred for use therewith, liquid or gaseous drying or separations agents could also be used if desired on a flow-through basis.

Differently-constructed probe members could be used which also feature a protected, externally-supported tubular membrane for providing an interface for mass transfer between the separations agent and the fluid to be treated thereby. The '932 patent for example, provides such an alternate probe member design at FIGS. 1–4.

Still further, it may be appropriate and desirable in some circumstances to employ a probe member of the type described in copending and commonly-assigned U.S. Ser. No. 07/986,838 (such application being incorporated herein by reference), filed concurrently herewith and entitled "Sample Probe With Temperature Monitoring And/Or Control", now allowed wherein a temperature monitoring device such as a thermocouple and a cartridge-type heater are preferably incorporated within the body of the probe member.

And while the apparatus of the present invention has been described for selectively removing a species from a fluid so that, for example, dry fluid of a high purity can be provided to an associated gas chromatograph or like apparatus, the apparatus of the present invention could also be used for determining the concentration of the species in a given fluid flowing through the tubular membrane.

All of this having been said,
What is claimed is:

1. A membrane-based fluid separations apparatus, comprising:

an outer vessel or outer vessel assembly having an opening defined therein;

a probe member inserted through and secured in the opening and having a groove defined therein; and a tubular membrane supported in the groove in the probe member and defining first and second ends which can be placed in fluid communication with a source of a fluid from which a species is to be selectively removed and a desired destination for fluid from said membrane, respectively.

2. An apparatus as defined in claim 1, further comprising a solid drying or other separations agent placed within the outer vessel or outer vessel assembly.

3. An apparatus as defined in claim 1, further comprising means for permitting a flow of a gaseous or liquid dessicant through the outer vessel or outer vessel assembly.

4. A membrane-based fluid separations apparatus, comprising:

an outer vessel or outer vessel assembly having first and second openings defined on first and second respective ends of the vessel or vessel assembly;

a removable end cap placed securely over the first opening whereby a drying or other separations agent placed or flowing within the vessel is contained by the end cap at said first end;

a probe member inserted through and secured in the second opening of the vessel or vessel assembly and having a groove defined therein; and a tubular membrane supported in the groove in the probe member and defining first and second ends which can be placed in fluid communication with a source of a fluid from which a species is to be selectively removed and a desired destination for fluid from said membrane, respectively.

5. An apparatus as defined in claim 4, further comprising a solid drying or other separations agent placed within the outer vessel or outer vessel assembly and contained by said end cap.

6. An apparatus as defined in claim 4, wherein the probe member is removable from the second opening.

7. An apparatus as defined in claim 4, further comprising means for purging unwanted gases from the outer vessel or outer vessel assembly.

8. An apparatus as defined in claim 4, wherein:

the groove in said probe member comprises a double-lead flight threaded portion of the probe member which is traversed by the membrane in alternating flights from a first end of the probe member to a second end thereof and back again, such alternating flights communicating via an S-shaped curve defined in said second end of said probe member; and further wherein the probe member defines internal channels therein at the first end which communicate with the alternating flights of the double-lead flight threaded portion of the probe member, and through which the membrane extends to define said first and second membrane ends.

9. An apparatus as defined in claim 8, wherein the double-lead flight threaded portion of the probe member and the tubular membrane supported therein extend substantially over the entire length of the probe member, from the second opening in the outer vessel or outer vessel assembly toward the first end of the outer vessel or outer vessel assembly.

10. An apparatus as defined in claim 8, wherein the tubular membrane is sized so as to be fully supported within the alternating flights of said double-lead flight threaded portion of said probe member.

11. An apparatus as defined in claim 4, wherein the tubular membrane is sized so as to be fully supported within the groove in said probe member.

12. An apparatus as defined in claim 4, wherein the probe member is constructed of a thermally conductive material and wherein the apparatus further comprises a heater placed within the probe member.

13. An apparatus as defined in claim 4, wherein the probe member is constructed of a thermally conductive material and wherein the apparatus further comprises a temperature monitoring device placed within the probe member.

* * * * *